(12) United States Patent
Calis et al.

(10) Patent No.: US 11,638,410 B2
(45) Date of Patent: May 2, 2023

(54) METHOD AND SYSTEM FOR CONTROLLING THE CLIMATE OF AN INSECT REARING CLIMATE AREA

(71) Applicant: Ynsect NL R&D B.V., Ermelo (NL)

(72) Inventors: Johannes Ignatius Maria Calis, Ermelo (NL); Robbert Dam, Zwolle (NL)

(73) Assignee: Ynsect NL R&D B.V., Ermelo (NL)

( * ) Notice: Subject to any disclaimer, the term of this patent is extended or adjusted under 35 U.S.C. 154(b) by 11 days.

(21) Appl. No.: 16/634,138

(22) PCT Filed: Jul. 23, 2018

(86) PCT No.: PCT/NL2018/050510
§ 371 (c)(1),
(2) Date: Jan. 25, 2020

(87) PCT Pub. No.: WO2019/022596
PCT Pub. Date: Jan. 31, 2019

(65) Prior Publication Data
US 2020/0205369 A1   Jul. 2, 2020

(30) Foreign Application Priority Data

Jul. 25, 2017   (NL) .................................... 2019344

(51) Int. Cl.
*A01K 1/00* (2006.01)
*A01K 67/033* (2006.01)
(52) U.S. Cl.
CPC .......... *A01K 1/0047* (2013.01); *A01K 67/033* (2013.01)
(58) Field of Classification Search
CPC ................ A01K 67/033; A01K 1/0047; A01K 1/0064; A01K 1/0076
See application file for complete search history.

(56) References Cited

U.S. PATENT DOCUMENTS 1,641,899 A * 9/1927 Nesdahl .................... F26B 9/06
454/236
4,085,705 A * 4/1978 Gland .................... A01K 1/031
119/418
(Continued)

FOREIGN PATENT DOCUMENTS

DE       2842974 A1 * 4/1980   ............. A01K 31/00
DE  102005028236 A1 * 1/2006   ........... A01K 31/005
(Continued)

OTHER PUBLICATIONS

English-language translation of FR 3046333 (Year: 2017).*
(Continued)

*Primary Examiner* — Monica L Perry
(74) *Attorney, Agent, or Firm* — Blank Rome LLP (57) ABSTRACT

A system controls the air climate in an insect rearing climate housing. The system has an insect rearing climate housing with clusters of one or more stacks of crates with insects. The crates have at least two ventilation openings associated with each crate. An aeration system has an air control unit with a database having a reference table with conditioned air properties in relation to input parameter(s). Aeration devices are connected to the air control unit adjacent to each stack of crates, and have a plurality of exit openings that provide airstreams over the insects. The method retrieves input parameter(s) for the air control unit per cluster of crates, the air control unit determines appropriate conditioned air properties of the airstreams based on the retrieved input parameter(s), and for each individual cluster of crates separately, the air control unit sets the determined conditioned air properties of the airstreams.

27 Claims, 4 Drawing Sheets

(56) References Cited

U.S. PATENT DOCUMENTS

| | | | | |
|---|---|---|---|---|
| RE32,113 E | * | 4/1986 | Harr | A01K 1/031 |
| | | | | 119/419 |
| 5,351,643 A | * | 10/1994 | Hughes | A01K 67/033 |
| | | | | 119/6.5 |
| 5,819,685 A | * | 10/1998 | Kappelt | A01K 67/033 |
| | | | | 119/6.5 |
| 8,181,604 B1 | * | 5/2012 | Avila | A01K 1/0052 |
| | | | | 119/448 |
| 9,462,795 B2 | * | 10/2016 | Chin | A01K 67/033 |
| 9,642,344 B2 | * | 5/2017 | Unger | A01K 67/033 |
| 10,405,528 B2 | * | 9/2019 | Comparat | B65G 1/0414 |
| 10,779,521 B2 | * | 9/2020 | Massaro | G06Q 50/02 |
| 10,842,138 B1 | * | 11/2020 | Lolley | A01K 29/005 |
| 2011/0139075 A1 | * | 6/2011 | Shapiro Ilan | A01K 67/033 |
| | | | | 119/6.5 |
| 2013/0305994 A1 | * | 11/2013 | Dubinsky | A01K 5/0275 |
| | | | | 119/51.11 |
| 2013/0319334 A1 | * | 12/2013 | Newton | A01K 29/00 |
| | | | | 119/6.5 |
| 2015/0136862 A1 | * | 5/2015 | Wolf, II | F24S 90/00 |
| | | | | 236/1 C |
| 2016/0066552 A1 | * | 3/2016 | Arsiwalla | A01K 1/0047 |
| | | | | 119/6.5 |
| 2016/0227726 A1 | * | 8/2016 | Priest | F04D 25/166 |
| 2018/0279563 A1 | * | 10/2018 | Wolfe | A01G 25/02 |
| 2022/0087234 A1 | * | 3/2022 | Donners | A01K 67/0338 |

FOREIGN PATENT DOCUMENTS

| | | | | | |
|---|---|---|---|---|---|
| FR | 2737770 A1 | * | 2/1997 | | F24F 11/0001 |
| FR | 3013561 A1 | * | 5/2015 | | A01K 67/033 |
| FR | 3046333 | | 7/2017 | | |
| KR | 101303664 B1 | * | 9/2013 | | |
| KR | 20160063587 A | * | 6/2016 | | |
| KR | 20160079414 A | * | 7/2016 | | |
| WO | WO-9222198 A1 | * | 12/1992 | | A01K 67/033 |
| WO | WO-2012/115959 A2 | | 8/2012 | | |
| WO | WO-2014/171829 A1 | | 10/2014 | | |
| WO | WO-2016166471 A1 | * | 10/2016 | | B65G 1/0414 |

OTHER PUBLICATIONS

English-language translation of WO 2016/166471 (Year: 2016).*
English-language translation of FR 2737770 (Year: 1997).*
English-language translation of KR 101303664 (Year: 2013).*
International Search Report and Written Opinion of PCT/NL2018/050510, dated Jul. 23, 2018, 11 pages.

* cited by examiner

METHOD AND SYSTEM FOR CONTROLLING THE CLIMATE OF AN INSECT REARING CLIMATE AREA

RELATED APPLICATIONS

This application is a national phase of PCT/NL2018/050510, filed on Jul. 23, 2018, which claims the benefit of Netherlands Application No. 2019344, filed on Jul. 25, 2017. The entire contents of those applications are hereby incorporated by reference.

TECHNICAL FIELD

The current invention relates to a method and a system for controlling the climate of an insect rearing climate area.

BACKGROUND ART

As the world population grows, so does the need for proteins suitable for consumption. Cattle feedlots are the traditional source of proteins for consumption. However, they require a vast amount of money and energy to raise and feed, to remove waste and to keep them healthy. Insects are a very suitable alternative to cattle feedstock. They offer an economical and sustainable solution to current issues with the production and distribution of proteins for consumption. Insect farming is much cheaper and requires much less energy than cattle farming. Much of this efficiency is a result of insects being exothermic. Insects obtain heat from the environment instead of having to create their own body heat like typical mammals do. Furthermore, feeding insects is cheap. Organic waste can for example feed large populations of insect larvae. Due to all these advantages, insect farming is gaining popularity. Besides being a good source of protein, insects also have a high nutritional value, probiotic potential and affordable price. Furthermore, they can have high concentrations of amino acids and certain vitamins such as vitamin B12, riboflavin, and vitamin A.

Many insects which have maggot and/or larval stages are suitable for insect farming. Mature larvae of different types of insects can be used as protein rich food for animals or humans. For example larvae from the *Pachnoda marginata*, also referred to as the *Pachnoda butana*, a beetle from the subfamily Cetoniina. Other examples may include:
- the *Alphitobius diaperinus*, a species of beetle in the family Tenebrionidae,
- the *Zophobas morio*, a species of darkling beetle, whose larvae are known by the common name superworm or Zophobas,
- the mealworm beetle, *Tenebrio molitor*, a species of darkling beetle, the larvae being known as mealworms,
- the housefly, *Musca domestica*, is a fly of the suborder Cyclorrhapha, which larvae are known as maggots,
- *Hermetia illucens*, the black soldier fly, is a common and widespread fly
- grasshoppers, insects of the order Orthoptera, suborder Caelifera,
- crickets family Gryllidae (also known as "true crickets"), are insects related to grasshoppers, well-known species of this family are *Gryllus campestris* (field cricket), *Acheta domesticus* (house cricket), and *Gryllodes sigillatus* (banded cricket),
- other insects such as *Bombyx mori, Achroia girsella, Schistocerca americana gregaria, Galleria mellonella, Locusta migratoria migratorioides*.

Most of these insects are holometabolous insects, i.e. including four life stages as an embryo or egg, a larva, a pupa, and an imago or adult. The first stage is from the fertilization of the egg inside the mother insect until the embryo hatches. The insect starts as a single cell and then develops into the larval form before it hatches. The second stage lasts from hatching or birth until the larva pupates. In most species this mobile stage is worm-like in form, and these larvae are thus frequently referred to as "worms". The third stage is from pupation until eclosion. In preparation for pupation, the larvae of many species construct a protective cocoon of silk or other material, such as its own accumulated faeces. In this stage, the insect's physiology and functional structure, both internal and external, change drastically. Adult holometabolous insects usually have wings and functioning reproductive organs. In principle, the insects are harvested when the larvae are mature, i.e. near the end of the second stage, just before they turn into a pupa.

In insect farming, two phases can generally be discerned: breeding and rearing. The term breeding refers to the natural process of reproduction, involving spawning—the process of releasing and depositing eggs—, and hatching—bringing forth larvae from the egg. It differs from the process of rearing insects, which refers to the process of tending insects from baby-larvae to mature larvae, and possibly also including pupating and emerging into fully grown insects.

In known breeding facilities adult insects including egg-laying mothers are held in containers, in which containers the egg-laying mothers receive food and spawn their eggs. The eggs will hatch, and the baby larvae will mature into mature larvae in the rearing stage. The mature larvae are removed to serve as protein rich food.

The crates which serve to hold the insects during rearing are usually defined by a bottom with a substantially rectangular perimeter and upstanding opposite front and rear walls, as well as opposite side walls. Usually at least two opposing walls have ventilation openings. Such openings allow conditioned air to be blown there through for forced aeration. A feed delivery system automatically delivers larval feed to selected culture crates, while a separate water delivery system may deliver water to the culture crates.

Control over the rearing of insects in order to prevent erratic yields is of great importance. Parameters that need to be controlled include for example the amount and type of food, and the timing of adding additional food.

Furthermore, the climate conditions such as the temperature, moisture, and ventilation need to be well-controlled. WO 2014/171829 discloses a method and system for breeding insects, using a plurality of stacked crates. A climate wall with openings at the same height as the openings in the stacked crates is disclosed. Air is blown into the wall and blown out of the openings over the crates. The air that is blown into the wall can be regulated in respect of various of its aspects, such as temperature, moist level, energy content, gas content, flow rate and volume, and/or pressure. The air that has been passed through the crates will have changed in composition. The used air that leaves the crates is collected in the corridor in front of the crates by a suction tube. The air so withdrawn is analysed, and the changed values in air composition and quality are used to determine the characteristics of the new air that is blown through the wall.

SUMMARY OF INVENTION

The present invention aims to provide an improved climate control system. Thereto, the present invention provides a method for controlling the air climate in an insect rearing climate housing with clusters of one or more stacks of crates with immature phases of insects, wherein the stacks of crates comprise at least two ventilation openings associated with each crate, wherein use is made of
    an aeration system, comprising
        an air control unit with a database, which database comprises a reference table with conditioned air properties in relation to one or more input parameters;
        aeration devices connected to the air control unit adjacent to each cluster of crates, the aeration devices comprising a plurality of exit openings, the exit openings being arranged for providing airstreams over the immature phases of insects through the ventilation openings in each individual crate,
wherein the method comprises the steps of
    a) retrieving one or more input parameters for the air control unit per cluster of crates (4),
    b) the air control unit determining appropriate conditioned air properties of the airstreams based on the retrieved one or more input parameters, and,
    c) for each cluster of crates separately, the air control unit setting the determined conditioned air properties of the airstreams.

Due to variations in the contents of the crates and especially per cluster of crates, a common air climate within a rearing climate housing may not be the most advantageous climate for an individual cluster of crates. By a) retrieving input parameters for the air control unit per cluster of crates, b) the air control unit determining the conditioned air properties of the airstreams based on the retrieved one or more input parameters, and c) for each individual cluster of crates separately, the air control unit setting the determined conditioned air properties of the airstreams, the rearing climate conditions of each individual cluster of crates can be adjusted to the needs of the insects in the individual clusters of crates. Individualized settings are advantageous because in any insect rearing climate housing comprising stacks of crates, there will be differences between the needs of insects in each individual cluster of crates. For example, the average age of the insects may be different for different clusters, or there may be variations in the amount of the insects in the crates. Furthermore, the amount of food and/or water that has been added may differ. All these parameters influence the optimal climate conditions that are required for an individual cluster of crates to provide for an optimal growth of the insects. For example, the insects are cooled by the evaporation of water, and therefore differences in added amounts of water will influence the temperature in the crates. Furthermore, the amount of heating and $CO_2$, ammonia, nitrous oxide and other gases that are produced especially depend on the age of the immature phases of insects.

Due to the abovementioned possible differences between the contents of the crates, it may be the case that one cluster of crates comprises immature phases of insects which only produce very little heat and/or gases, while an adjacent cluster of crates comprises immature phases of insects that produce a lot of heat and/or gases. The first mentioned cluster of crates will require a minimal amount of cooling and/or minimal removal of produced gases, whereas the adjacent cluster requires significant cooling and/or removal of produced gases. In prior art methods for controlling the air climate in an insect rearing climate housing the individualised settings needed to accommodate these differences have not been possible.

Thus, according to the invention, the climate conditions for each individual cluster of crates are controlled separately. In this way the climate, including e.g. air temperature, composition and ventilation rate can be adjusted according to the needs of each individual cluster of crates. Thus, it is an advantage of the present invention that control is provided over the rearing of insects. It is another advantage that control is provided over the rearing parameters in individual cluster of crates. It a further advantage of the current invention that a more versatile system is provided. It is an even further advantage of the present invention that control over the climate conditions of each individual cluster of crates is provided separately. It is an even further advantage of the present invention that a climate system is provided based on one or more improved input parameters.

Furthermore, the present invention provides in combination:
    an insect rearing climate housing for rearing insects comprising clusters of one or more stacks of crates adapted to contain immature phases of insects, wherein the stacks of crates comprise at least two ventilation openings associated with each crate, and
    an aeration system, comprising
        an air control unit with a database, which database comprises a reference table with conditioned air properties in relation to one or more input parameters;
        aeration devices connected to the air control unit adjacent to each cluster of crates, the aeration devices comprising a plurality of exit openings, the exit openings being arranged for providing airstreams over a containment volume in each crate through the ventilation openings associated with each individual crate, wherein
the air control unit is adapted to
    determine the appropriate conditioned air properties of the airstreams based on the one or more input parameters, and to,
    for each cluster of crates separately, set the determined conditioned air properties of the airstreams.

This combination is adapted to perform the method of the current invention. Because the air control unit is adapted to determine the appropriate conditioned air properties of the airstreams based on the one or more retrieved input parameters, and to, for each individual cluster of crates separately, set the determined conditioned air properties of the airstreams, the rearing climate conditions of each individual cluster of crates can be adjusted separately as described above. A cluster of crates may consist of one or multiple adjacent stacks of crates in which the immature phases of insects have about the same composition (i.e. same age, amount of insects and amount of food and water that was fed to the insects, and the climate conditions that were experienced by the immature phases of insects over time).

DESCRIPTION OF EMBODIMENTS

Preferably, in the method according to the present invention, the one or more input parameters comprise an air property of the air directly above the immature phases of insects inside one of the crates. The properties of the air directly above the immature phases of insects provides for an accurate indication of the air climate that is experienced by the immature phases of insects inside a crate and inside each crate in the corresponding cluster of crates, assuming that the contents in each crate in the cluster of crates have a similar composition, i.e. the immature phases of insects have the same age and have been fed a similar type and amount of food and water, and have experienced the same climate conditions. By using the air property or properties directly above the immature phases of insects as an input parameter for the air control unit, the desired conditioned air properties for each cluster of crates can be determined more accurately. Preferably, a cluster of crates consists of a single stack of crates.

In a preferred embodiment of the method of the present invention, the one or more input parameters comprise the air temperature directly above the immature phases of insects inside one of the crates. From prior art methods, it is known that used air that leaves the crates can be collected in the corridor in front of multiple stacks of crates by a suction tube. The properties of this air can be used as input parameters for the regulation of the climate wall. However, the air temperature directly above the immature phases of insects provides for a significantly more accurate indication of the air temperature that is experience by the immature phases of insects inside a crate and inside each crate in the corresponding cluster of crates. By using the air temperature directly above the immature phases of insects in one crate of the cluster of crates as an input parameter for the air control unit, the appropriate conditioned air properties for each cluster of crates can be determined more accurately. This results in an increased optimization of the properties of the airstreams, and as a consequence in optimization of the insect rearing climate. The improved insect rearing climate conditions lead to a better growth of the insects and higher yields.

Preferably, the conditioned air properties comprise the conditioned air temperature. Initially, i.e. at the start of the lifecycle of the larvae, the insects generate little heat, and the conditioned air temperature can be maintained at a steady value, e.g. between 28° C. and 34° C. After several days of growth, the insects start to generate heat, possibly by an increased food uptake as well as by fermentation of the faeces and daily provided food. By setting the determined conditioned air properties, i.e. regulating the temperature of the airstreams, the increase in the air temperature can be counteracted. The temperature of the airstreams is preferably between 21° C. and 42° C., more preferably between 24° C. and 42° C. At lower temperatures condensation may occur. Condensation on equipment reduces the lifetime of the equipment due to possible rust formation and is therefore not desired. The temperature inside the crates may not be higher than 42° C., as higher temperatures will lead to adverse growing effects of the immature phases of insects. As the insects generate heat, a temperature of the airstreams higher than this value will lead to the temperature inside the crates being higher than 42° C. More preferably, the temperature of the airstreams is between 21° C. and 42° C., more preferably between 28° C. and 32° C. When the airstreams have a temperature within this range, the average temperature inside the climate housing will be between 28° C. and 38° C. This is an optimum temperature for the rearing of immature phases of insects. Most preferably, the temperature of the airstreams is 30° C. The airstreams may be cooled by a cooling device in order for the airstreams to acquire the required temperature.

In a preferred embodiment, the conditioned air properties comprise the conditioned air volumetric rate. A skilled person understands that a certain degree of cooling can be reached by generating airstreams with a certain volumetric rate. A stream of conditioned air with a high volumetric rate may have a higher temperature than a stream of conditioned air that is blown over the immature phases of insects with a lower volumetric rate. Both airstreams will obtain the same degree of cooling of the immature phases of insects inside the crates. Regulation of the air volumetric rate may also be used to influence other properties of the air climate, such as the humidity, level of oxygen, level of carbon dioxide, etc. If for example a higher level of oxygen is required, this can be achieved by a high volumetric rate of airstreams with an oxygen level that is slightly higher than the current oxygen level, or it can be achieved by a lower volumetric rate of airstreams which are very enriched with oxygen as compared to the current oxygen level.

In an embodiment, the one or more input parameters comprise the age of the immature phases of insects. The amount of heat and gases, such as carbon dioxide, that are produced by the immature phases of insects depend on the age of the immature phases of insects. Initially, the immature phases of insects do not produce a significant amount of heat. After some time, e.g. several days or weeks, depending on the type of insect, the immature phases of insects start to produce heat. A higher amount of heat is produced in the latter stages before the larvae are mature. By using the age of the immature phases of insects as an input parameter for the air control unit, the heat that is generated by the immature phases can be anticipated on, and the conditioned air properties of the airstreams can be set accordingly.

In another embodiment, the one or more input parameters comprise the time of feeding of the immature phases of insects. Feeding of the insects will result in the production of heat and gases by the insects, as the food is consumed and digested. The production of heat will gradually increase, starting from the moment of feeding of the insects, to the moment that the insect food is most actively being digested. Thus, some time after feeding of the insects, a maximum heat production related to digestion of food by insects can be observed. The peak of this heat production can be predicted based on the feeding time. Therefore, the time of feeding of the immature phases of insects can suitably be used as an input parameter for the air control unit. By using the time of feeding of the immature phases of insects as an input parameter for the air control unit, the heat that is generated by the immature phases can be anticipated on, and the conditioned air properties of the airstreams can be set accordingly.

Preferably, the one or more input parameters comprise the humidity directly above the immature phases of insects inside one of the crates. The relative humidity preferably has a value between 55% and 80%. Deviations of the humidity of the air can be compensated by setting the humidity of the airstreams accordingly. Thus, in the method according to the invention, preferably the conditioned air properties comprise the humidity.

In an embodiment, the one or more input parameters comprise the level of carbon dioxide directly above the immature phases of insects inside one of the crates. The production of carbon dioxide or $CO_2$ by the immature phases of insects is high. The $CO_2$ level is preferably kept below 3500 ppm in order to create adequate working conditions for employees of the insect rearing facility and possibly to obtain good insect growth. A high production of carbon dioxide by the immature phases of insects should be counteracted by airstreams with a relatively low level of carbon dioxide compared to the level of carbon dioxide directly above the immature phases of insects inside one of the crates.

Preferably, the one or more input parameters comprise the level of oxygen directly above the immature phases of insects inside one of the crates. The immature phases of insects need oxygen for their survival. If the oxygen level drops too much, this adversely affects the growth of the immature phases of insects. Therefore, the oxygen level should be monitored, and if needed adjusted according to the current needs of the immature phases of insects. Thus, preferably the conditioned air properties comprise the level of oxygen.

In a preferred embodiment the airstreams comprise components selected from the group consisting of: medication, appetite stimulants, and/or toxins. Such components can advantageously be used to influence the growth of the immature phases of insects. Medication may for example decrease the influence of harmful food ingredients. As a result, food of a lesser quality may be used for the immature phases of insects, while still leading to adequate growth of the immature phases of insects and good quality of the nutrients that are won from the matured phases of insects. Appetite stimulants may increase the growth rate of the immature phases of insects. This may lead to the immature phases of insects taking up more food, and thus in a higher production of nutrients from the mature larvae, which matured insects may have a higher body weight than mature larvae that have not been subjected to appetite stimulants. Additionally or alternatively, appetite stimulants may lead to an increased growth rate of the immature phases of insects. An increased growth rate is advantageous as it increases the production rate of nutrients from matured phases of insects.

In a preferred embodiment of the method according to the invention, the airstreams are turbulent streams. Turbulent streams are very effective for mixing air with different properties. Thus the properties of the airstreams are effectively transferred to the air directly above the immature phases of insects.

Alternatively, the airstreams are laminar streams. The production of a laminar stream of conditioned air requires less energy for producing the stream of air than the production of a turbulent stream of conditioned air.

In a further preferred embodiment of the method of the invention, the volumetric rate of the airstreams is an average volumetric rate, and varies between a periodically reoccurring maximum and minimum. The periodically reoccurring maximum and minimum may be achieved by varying the volumetric rate of the airstreams according to a pattern. For example, the airstreams over the immature phases of insects may be oscillating airstreams. This can for example be accomplished by a rotating fan. The maximum volumetric rate is then achieved when the fan is aimed at the crates, and the minimum rate is achieved when the fan is aimed away from the crates. Alternatively, the varying of the volumetric rate of the airstreams over the immature phases of insects can be accomplished by periodically moving the air exit direction of the exit openings, preferably by moving the air exit direction of the exit openings according to a periodically reoccurring pattern. In order to accomplish this, the exit openings are preferably rotatable, such as rotatable nozzles or slits. Further alternatively, or even in addition to periodically moving the air exit direction of the exit openings, this can be accomplished by varying the air pressure of the airstreams.

It has been found that the periodically varying volumetric rate of the airstreams over the immature phases of insects not only results in movement of air over the individual crates, but also results in movement of the air between the stacks of crates, which provides a significant improvement in the overall temperature regulating abilities of the aeration system.

A similar effect of movement of the air between the stacks of crates may be achieved by varying the temperature of the airstreams between a periodically reoccurring maximum and minimum. Thereto, the temperature of the airstreams preferably is an average temperature, and varies between a periodically reoccurring maximum and minimum.

Preferably, the method according to the invention, further comprises a step d) of discharging warm air from above the immature phases of insects and capturing the heat of the warm air with a heat storage device. Capturing this heat instead reduces waste of energy. The captured heat stored in the heat storage device is preferably used to heat the airstreams.

Preferably, in the combination of the present invention, the air control unit further comprises one or more sensors, which are arranged in the direct vicinity of the containment area of one of the crates. Preferably the sensors are arranged in or directly above the containment area of one of the crates. The sensors can measure properties of the air, and can provide one or more input parameters for the air control unit. By placing the one or more sensors in the direct vicinity of the containment area of one of the crates, adequate input parameters for the air control unit can be determined. This as opposed to for example placing the sensors at a location more distant from the contents of the crates. The properties of the air at a distant location may not reflect the properties of the air directly above the containment area of the crates.

In embodiments, the one or more sensors comprise a temperature sensor, a humidity sensor, an oxygen sensor, and/or a carbon dioxide sensor.

In embodiments, the plurality of exit openings are nozzles. In alternative embodiments, the plurality of exit openings are horizontal slits for providing a lamellar stream of air.

Preferably, the database comprises a management executing system (MES). In such a case, the MES comprises storage information with respect to the location and contents of the clusters of crates and/or each individual stack of crates.

Preferably, the combination according to the current invention further comprises a heat storage device.

DETAILED DESCRIPTION OF EMBODIMENTS

Figure 1A:
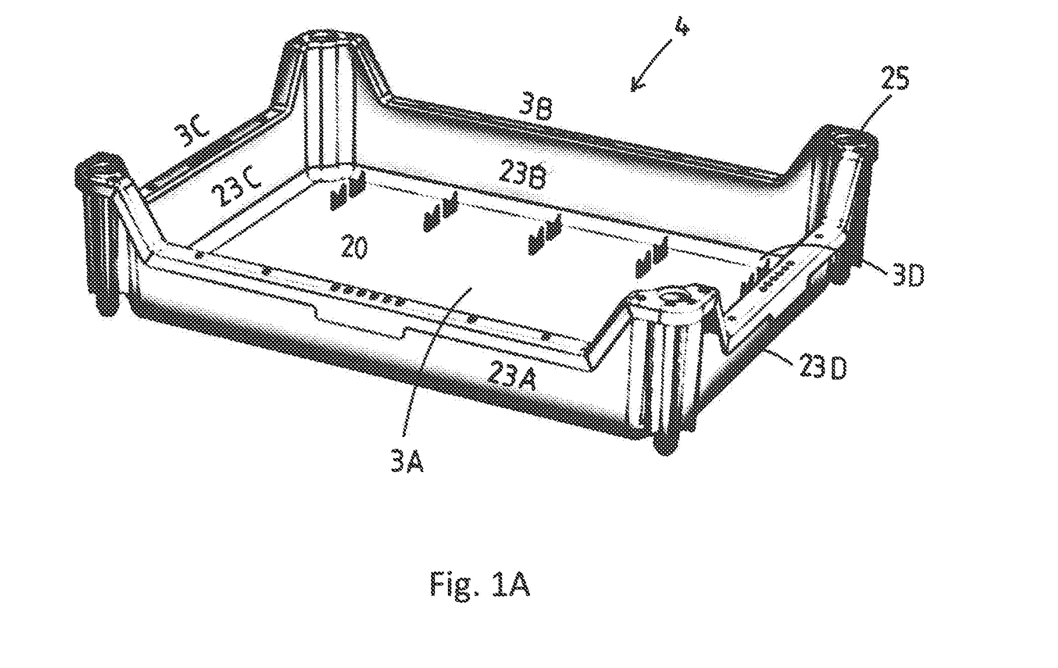
FIG. 1A is a perspective view of an embodiment of an individual crate.

FIG. 1A illustrates an embodiment of an individual crate 4. The depicted crate 4 is an open topped, stackable container, which is advantageously made from moulded plastic. The crate 4 is rectangular with a bottom 20 and upstanding front and rear walls 23A, 23B, and opposite side walls 23C, 23D. The walls are joined to the bottom 20. They are joined to other walls via corner structures 25. Each of the walls 23 have ventilation openings 3, here formed by a recess in the upper edge of the walls 23. However, differently shaped ventilation openings are conceivable. For example the opposing front and rear walls 23A, 23B and/or the opposing side walls 23C, 23D may comprise multiple circular or rectangular openings which are suitable for allowing an airflow from one opening through to another opening. Other opening shapes are conceivable as well, even as openings which comprise a mesh or other filtration material. In some embodiments, an airstream 31 may enter through one of the ventilation openings 3 and leave through an opening in the opposing wall, whereas in other embodiments the airstream 31 may leave through an opening in a joining wall 23.

The shape and location of the ventilation openings 3 is not particularly limited as long as the openings are suitable for allowing a stream 31 of conditioned air to flow over a containment volume 6 of the crate 4. The containment volume 6 is defined as the volume that is confined between the bottom of the crate 4, the four walls 23, and an imaginary plane parallel to the bottom of the crate 4. It is possible to design a crate 4 comprising only a bottom 20, corner structures 25, and a mesh or other porous structure, stretched between the corner structures. In principle this allows air to flow through the entire crate 4 when empty. Therefore, the skilled person will understand that the containment volume 6 of the crate 4 is a variable, the size of which depends on the actual volume of the content of immature phases of insects of the crate 4.

Figure 1B:
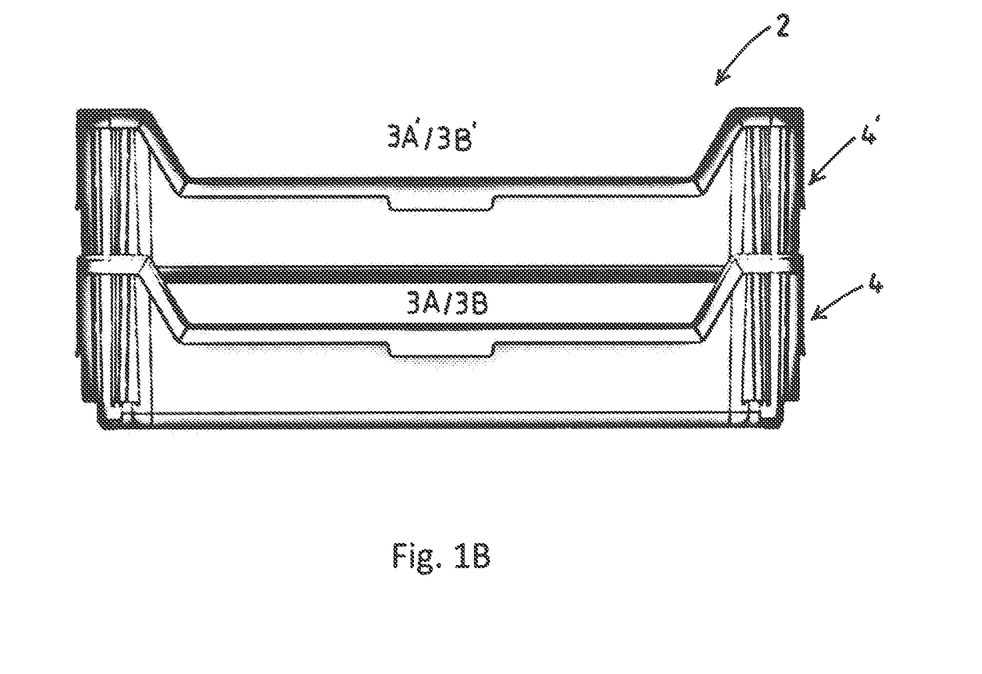
FIG. 1B is a plan view of a stack of two crates of FIG. 1A.

FIG. 1B illustrates a stack 2 of two of the crates 4 of FIG. 1A. The stack 2 of crates 4 comprises ventilation openings 3A and 3A' horizontally opposing the ventilation openings 3B and 3B', as well as opposing side wall ventilation openings 3C, 3D (visible in FIG. 1A). In order to comply with the present invention, one set of (i.e. at least two) ventilation openings associated with each crate 4 is minimally required. The set of ventilation openings 3 may be horizontally opposing, but an air stream 31 may also leave through an exit opening (e.g 3C) in the wall adjacent to the entry opening (e.g. 3A).

Figure 3A:
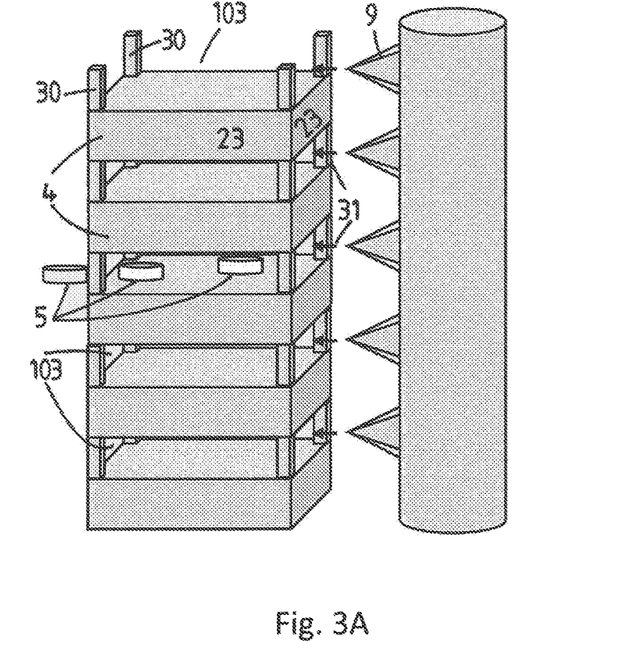
FIG. 3A is a perspective view of stacks of crates and aeration devices with nozzle-shaped exit openings.
Figure 3B:
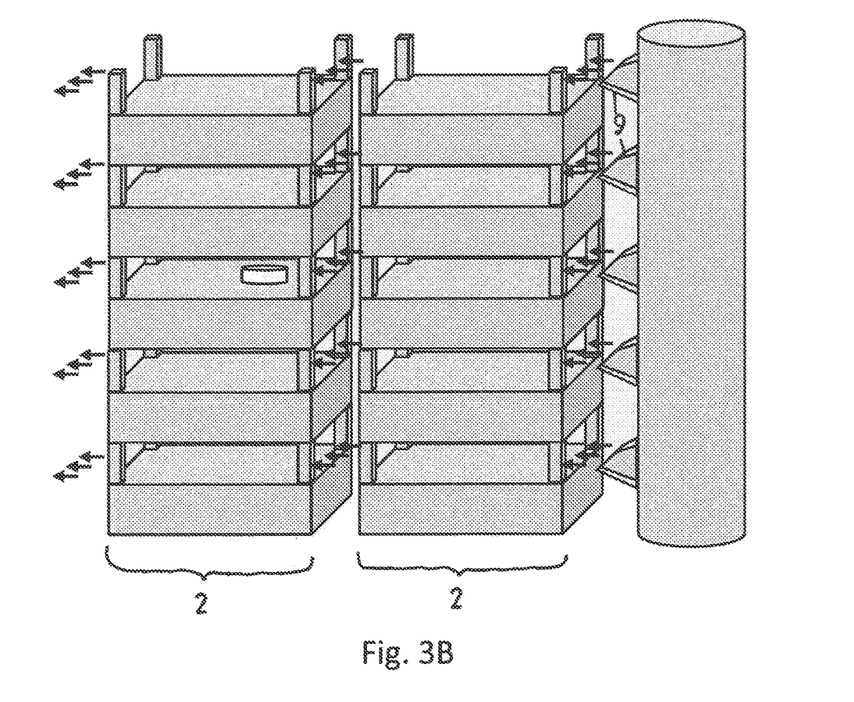
FIG. 3B is a perspective view of stacks of crates and aeration devices with slit-shaped exit openings.

It is also conceivable that an individual crate 4 itself does not comprise any ventilation openings. FIGS. 3A and 3B depict other embodiments of the invention. The crates 4 are basic crates 4 defined by a bottom 20, four vertically upstanding side walls 23 and an open top 24. Pillars 30 are provided between the crates 4 in a stack 2. This results in ventilation openings 103 associated with each individual crate 4 in a stack 2 of crates 4. In this case the containment volume 6 is defined as the volume enclosed by the bottom 20, side walls 23 and open top 24 of the crate 4. A set of two pillars 30 may be joined by a joining portion to form a panel.

Figure 2:
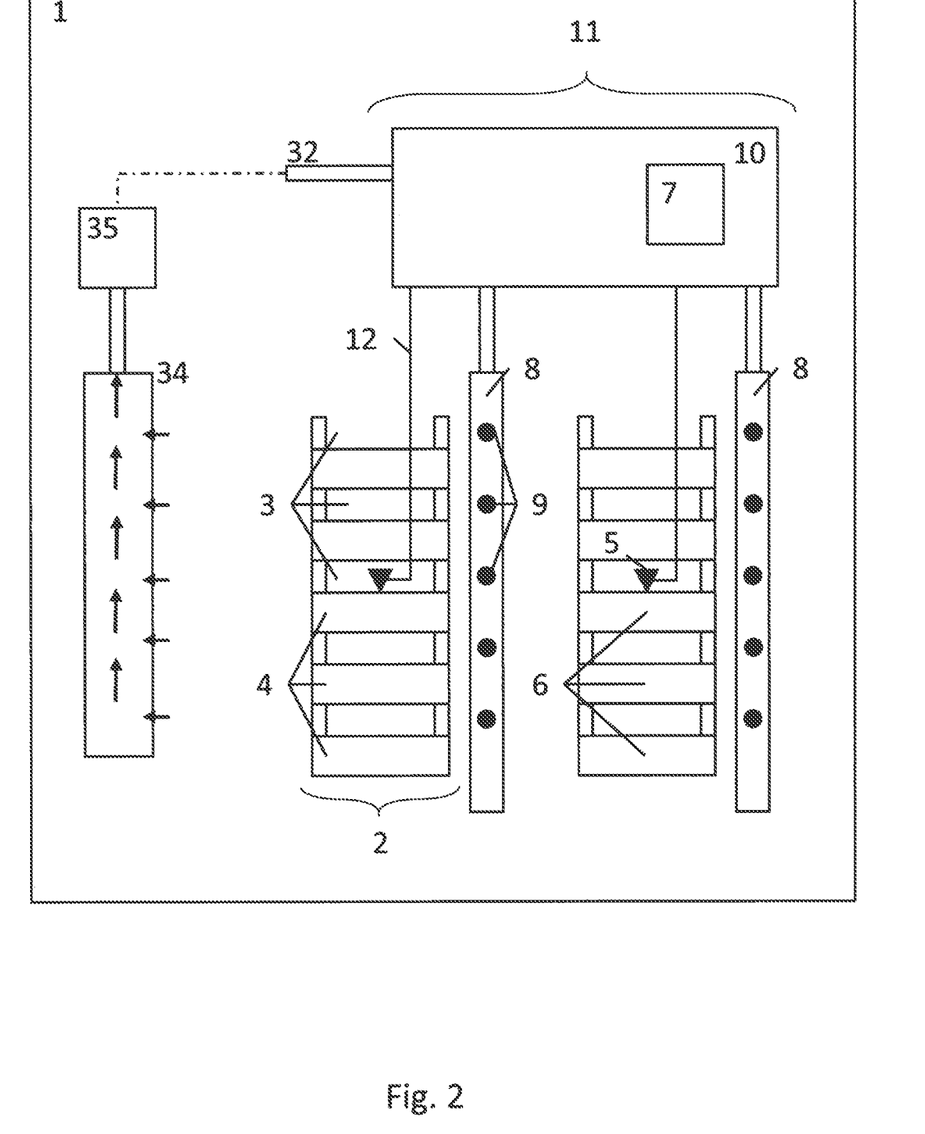
FIG. 2 is a schematic illustration of an insect rearing climate housing and aeration system.

FIG. 2 further depicts an insect rearing climate housing 1. The insect rearing climate housing 1 can be a greenhouse, factory hall, building, room, or otherwise enclosed space suitable for accommodating stacks 2 of crates 4. Inside the climate housing 1, vertical stacks 2 of crates 4 adapted to contain immature phases of insects are arranged next to each other, for example in a row or several rows. Although the figure only shows a limited number of stacks 2 of crates 4 and only one parallel row, it should be understood that preferably and advantageously many of stacks 2 of crates 4 will be present in an actual production facility. Several stacks 2 of crates 4 with immature phases of insects with about the same composition (i.e. same age, amount of insects and amount of food and water that was fed to the insects) may be placed adjacently to form a cluster of crates. An aeration system 11 comprises an air control unit 10 with a database 7, and aeration devices 8 with exit openings 9. Each stack 2 of crates 4 in a cluster may have a corresponding aeration device 8.

The air control unit 10 may be placed inside the climate housing 1, or it may be placed outside of the climate housing 1. For example the air control unit 10 can be placed on the roof of the insect rearing climate housing 1 or in an adjacent room, hall or other space. The air control unit 10 is adapted to determine appropriate conditioned air properties of streams 31 of conditioned air based on one or more input parameters, and for each individual cluster of crates 4 separately, to set the determined conditioned air properties of the streams 31 of conditioned air. The air control unit 10 comprises an air inlet 32. It may further comprise a fan, air pump or other air displacing means for displacing air towards the exit openings 9 of the aeration devices 8, a valve system for creating individual streams of air, and several means for adjusting air settings, such that each individual stream of air can be set to have different properties. The means for adjusting air settings may for example be a supply of oxygen, such as an oxygen cylinder, an air moisturizer and heating means.

The database 7 may be a computer which can either be an integral part of the air control unit 10, or it may be connected to the air control unit 10 and placed at a different location. For example, the air control unit 10 may be placed on top of an insect rearing climate housing 1, whereas the database 7 is placed inside the insect rearing climate housing 1, or in an adjacent room or facility. The database 7 may be a computer which is placed in an easily accessible location, such that a user may easily access the database 7. Additionally or alternatively, the database 7 may have remote access possibilities. The database 7 is preferably coupled to an MES (Management Executing System). The MES may separately comprise storage information with respect to the location and contents of the stacks 2 of crates 4. The MES may further contain information regarding to the process planning, feeding recipes, routing per process and control over the equipment. Aeration devices 8 with exit openings 9 are connected to the air control unit 10. The aeration devices 8 may comprise cylindrical or rectangular vertical pipes, hoses, tubes or other means suitable for passing a stream of air. The aeration devices 8 may be specifically designed to comprise nozzle placement openings, adapted to place specifically constructed and easily replaceable nozzles 9 for optimal ventilation. In the shown configuration, the aeration devices 8 are arranged next to stacks 2 of crates 4. At least one aeration device 8 is associated with a cluster of crates 4. Preferably, at least one aeration device 8 is associated with a stack 2 of crates 4, and it is even also conceivable that multiple aeration devices 8 are associated with a single stack 2 of crates 4. In that case, the different aeration devices 8 may each provide streams 31 of conditioned air with different properties through the exit openings 9. Alternatively, each aeration device 8 associated with a stack 2 of crates 4 provides streams 31 of conditioned air with identical properties, i.e. all having the same temperature, oxygen content, etc.

FIG. 3A illustrates exit openings 9 in the form of nozzles. FIG. 3B illustrates exit openings 9 in the form of slits. The exit openings 9 are evenly spaced and correspond with ventilation openings 103 on one side of the stack 2 of crates 4. The exit openings 9 are aligned with the respective ventilation openings 103 of the individual crates 4, such that streams 31 of conditioned air can be guided over a bed of substrate contained in each crate 4 upon leaving the respective exit opening 9. It is also possible that multiple stacks 2 of crates 4 belonging to a cluster of crates 4 are arranged side by side, such that the ventilation openings 3 of the stacks are aligned for allowing the airstreams 31 to pass over multiple crates. This is shown in FIG. 3B. Streams 31 from the nozzles in FIG. 3A are turbulent streams, whereas streams 31 from the slit shaped exit openings 9 in FIG. 3B indicate mainly laminar streams. While the crates 4 are shown empty, it will be understood that these will each be filled with an appropriate amount of food and insect larvae, when the aeration system 10 is in operation.

FIGS. 3A and 3B further illustrate sensors 5 which are arranged in the direct vicinity of the containment volume 6 of one of the crates 4. It will be understood that the sensors 5 can be located within the containment volume, slightly above the containment volume, or next to an opening 103 at the opposite side of the aeration device 8, or at the side adjacent to the side of the aeration device 8, depending on the direction of the airstream 31. When placed in the latter position, the air properties measured by the sensors 5 will reflect the properties of the air directly above the containment volume 6, because of the movement of the air in the direction of the airstreams 31 from above the crates 4 over the sensors 5. Preferably, the sensors 5 are placed in or directly above the containment volume. Any combination of insect rearing climate housing and aeration system according to the invention can comprise one or more sensors 5. The sensors 5 can be one or more of: a temperature sensor, oxygen sensor, carbon dioxide sensor, humidity sensor, air flow volumetric rate sensor, etc. For each type of sensor that is chosen to be present in the system, at least one sensor 5 is present per cluster 2 of crates 4. More sensors 5 of the same type per cluster 2 of crates 4 can be used for an increased accuracy of measurements. For example, a sensor 5 such as a temperature sensor may be present per stack 2 of crates 4 in a cluster of multiple stacks 2 of crates 4. In this way the temperature is measured for each individual stack, and the corresponding values can be averaged to obtain the average temperature in a cluster of crates 4. Even per stack 2 of crates 4, multiple sensors of the same type may be present. For example, a sensor associated with one of the top crates 4 may be present, together with a temperature sensor associated with one of the middle crates 4, and one associated with one of the bottom crates 4. The corresponding measured values can be averaged.

The aeration system 11 according to the invention can further comprise a suction device 34 such as a suction tube for collecting streams 31 of air that leave the crates 4. Additionally, the aeration system 11 may comprise a heat storage device 35.

Figure 4:
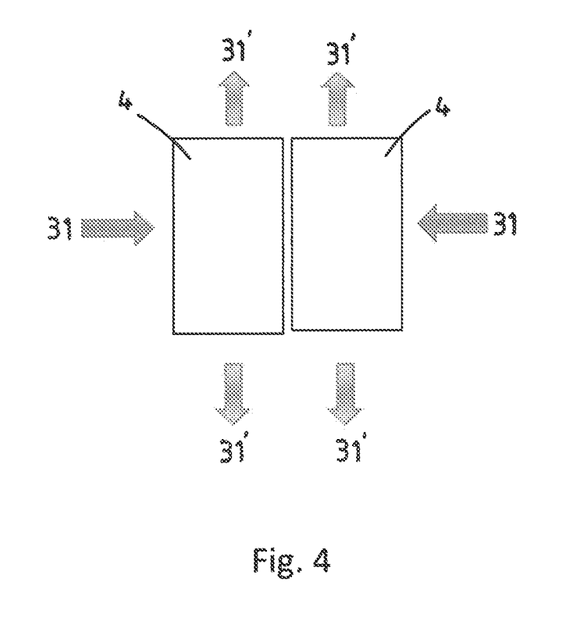
FIG. 4 is a top view illustrating the flow of the airstreams in an alternative embodiment of the invention.

FIG. 4 illustrates an embodiment in which airstreams 31 enter through one of the ventilation openings 3 and leave via arrow 31' through an opening in a joining wall 23.

In an embodiment of the method and system according to the invention, eggs of the same age are collected from egg-laying mothers, and placed in crates 4. Generally, the eggs in a single crate 4 will hatch into baby larvae at about the same time, and each crate 4 contains larvae which have the same age measured in days. Crates 4 with larvae of the same age are stacked on top of each other to form a stack 2 of crates 4. Periodically, for example one or more times a day, food is placed within each crate 4. Typical insect foods are vegetables and fruits such as apples, (plant-based) protein rich food, and grain products, and byproducts such as wheat bran, brewery spent grain, and poultry feed. The larvae will consume the food and as a consequence grow in size. Another consequence is the production of heat, as well as carbon dioxide gas and other waste gases and solids. It has been found that the production of heat, gases and solids can be predicted based on the time of feeding. Waste solids, e.g. defecation as well as leftover food are preferably periodically removed from the crates 4.

It has furthermore been found that depending on the age of the larvae, different degrees of heat are produced. For example, for about the first two weeks of the larva life cycle of a type of beetle, the larvae do not produce a significant amount of heat. In the third week heat is produced, and in the week up to harvesting the mature larvae, a significant amount of heat is produced.

Therefore, the age can be used as an input parameter for the air control unit 10. The age of the larvae may for example be determined by an operator who determines the date that the eggs hatched based on information written on a crate 4 or contained in a barcode on the crates 4. Alternatively, this information may be read from a barcode or RFID chip automatically after which this information is fed to the air control unit 10. Such information may alternatively be acquired from the MES. On the basis of the age of the larvae and the reference table with conditioned air properties in relation to one or more input parameters in the database 7, the air control unit 10 determines the appropriate conditioned air properties of the streams 31 of conditioned air based on the age, and for each individual cluster of crates 4 separately, the air control unit 10 sets the determined conditioned air properties of the airstreams.

For proper growth, the temperature above the immature phases of insects is kept stable between 28° C. and 34° C., preferably between 29 and 31° C., for example at 30° C. Thereto appropriate conditioned air properties of the streams 31 of conditioned air comprise a conditioned air temperature between 21 and 42° C., preferably between 24 and 42° C. In the initial life stage wherein the larvae do not produce a significant amount of heat, the temperature of the streams 31 of conditioned air mainly depends on the temperature outside of the insect rearing climate housing. On summer days, cooling may be required, whereas during winter, heating will be required. Preferably, the conditioned air temperature of the streams 31 of conditioned air is between 21 and 32° C., more preferably between 28° C. and 32° C., such as 30° C.

Additionally or alternatively, the air temperature directly above the immature phases of insects inside one of the crates 4 may be measured with a temperature sensor 5. Other suitable sensors include a humidity sensor, an oxygen sensor, a carbon dioxide sensor, and/or a flow sensor. Such a sensor or sensors 5 is/are connected via at least a data communication line 12 to the air control unit 10 comprising database 7. The database 7 comprises a reference table with conditioned air properties in relation to the input parameters, i.e. the determined age of the larvae, and/or the measured temperature, the measured humidity level, the measured oxygen level, the measured carbon dioxide level, the measured flow rate, etc. Based on the combination of the measured properties, i.e. the retrieved input parameters, the database 7 returns the appropriate conditioned air properties of the streams 31 of conditioned air. For example, in the case of a temperature sensor combined with an oxygen sensor, and additional knowledge about the age of the larvae, the database will return an appropriate setting for the air control unit 10 based on the combination of these three parameters. The air control unit 10 then sets the determined conditioned air properties of the airstreams.

Via the air inlet 32, the air control unit 10 acquires air of which the properties can be adjusted to match the determined conditioned air properties. The air may for example be withdrawn from within the insect rearing climate housing, or it may be fed to the system from outside of the insect rearing climate housing, e.g. drafted from the outside air. In case of withdrawn air from the climate housing 1, it can be analysed so that its properties may be adjusted as necessary for reuse in the system. A combination of outside air and withdrawn air is also possible.

By the use of the one or more air displacing means within the system, the air is displaced from the air inlet 32 towards the exit openings 9 of the aeration devices 8. By the valve system, several individual streams of air are created. The properties of each individual stream of air are adjusted by means for adjusting air properties, thereby creating streams 31 of conditioned air. The aeration devices 8 are preferably operable to vary the volumetric rate and/or temperature of the airstreams 31 between a periodically reoccurring maximum and minimum.

The streams 31 of conditioned air are then blown out of exit openings 9. The streams 31 of conditioned air will either be lamellar or turbulent. It is conceivable that one of the two is desired under given circumstances.

The system can additionally comprise a heat storage device 35.

As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in any appropriately detailed structure. Further, the terms and phrases used herein are not intended to be limiting, but rather, to provide an understandable description of the invention.

The terms "a"/"an", as used herein, are defined as one or more than one. The term plurality, as used herein, is defined as two or more than two. The term another, as used herein, is defined as at least a second or more. The terms including and/or having, as used herein, are defined as comprising (i.e., open language, not excluding other elements or steps). Any reference signs in the claims should not be construed as limiting the scope of the claims or the invention.

The mere fact that certain measures are recited in mutually different dependent claims does not indicate that a combination of these measures cannot be used to advantage.

The invention claimed is:

1. A method for controlling the air climate in an insect rearing climate housing with
    clusters of one or more stacks of crates with immature phases of insects, wherein the one or more stacks of crates comprise at least two ventilation openings associated with each of the crates, wherein use is made of an aeration system, comprising
        a sensor measuring a property of the air directly above the immature phases of insects inside one of the crates of each of the clusters of crates, the sensor being connected via at least a data communication line to an air control unit;
        the air control unit with a database, which database comprises a reference table with conditioned air properties in relation to one or more input parameters, wherein the one or more input parameters comprise the measured property of the air directly above the immature phases of insects inside one of the crates;
        aeration devices connected to the air control unit adjacent to each of the clusters of the one or more stacks of crates, the aeration devices comprising a plurality of exit openings, the exit openings being arranged for providing airstreams over the immature phases of insects through the ventilation openings in each of the crates,
    wherein the method comprises the steps of
        a) retrieving, from the measured property of the air, the one or more input parameters for the air control unit per cluster of crates,
        b) the air control unit determining from the reference table of the database appropriate conditioned air properties of the airstreams based on the retrieved one or more input parameters, and
        c) for each of the clusters of the one or more stacks of crates separately, the air control unit setting the determined appropriate conditioned air properties of the airstreams.

2. The method according to claim 1, wherein the one or more input parameters comprise the air temperature directly above the immature phases of insects inside one of the crates.

3. The method according to claim 1, wherein the one or more input parameters comprise the humidity directly above the immature phases of insects inside one of the crates.

4. The method according to claim 1, wherein the one or more input parameters comprise the level of carbon dioxide directly above the immature phases of insects inside one of the crates.

5. The method according to claim 1, wherein the one or more input parameters comprise the level of oxygen directly above the immature phases of insects inside one of the crates.

6. The method according to claim 1, wherein the one or more input parameters comprise the age of the immature phases of insects.

7. The method according to claim 1, wherein the one or more input parameters comprise a time of feeding of the immature phases of insects.

8. The method according to claim 1, wherein the air control unit sets the temperature of the airstreams.

9. The method according to claim 8, wherein the temperature of the airstreams is an average temperature, and varies between a periodically reoccurring maximum and minimum.

10. The method according to claim 1, wherein the air control unit sets the volumetric rate of the airstreams.

11. The method according to claim 10, wherein the volumetric rate of the airstreams is an average volumetric rate, and varies between a periodically reoccurring maximum and minimum.

12. The method according to claim 11, wherein the periodically reoccurring maximum and minimum are achieved by varying the air pressure of the airstreams.

13. The method according to claim 1, wherein the air control unit sets the humidity of the airstreams.

14. The method according to claim 1, wherein the air control unit sets the level of oxygen of the airstreams.

15. The method according to claim 1, wherein the airstreams comprise components selected from the group consisting of: medication, appetite stimulants, and toxins.

16. The method according to claim 1, wherein the airstreams are laminar streams.

17. The method according to claim 1, wherein the airstreams are turbulent streams.

18. The method according to claim 1, further comprising a step d) of discharging warm air from above the immature phases of insects and capturing the heat of the warm air with a heat storage device.

19. The method according to claim 18, wherein the temperature of the airstreams is at least partially achieved by warming ambient air using the heat stored in the heat storage device.

20. In combination:

an insect rearing climate housing for rearing insects comprising clusters of one or more stacks of crates adapted to contain immature phases of insects, wherein the one or more stacks of crates comprise at least two ventilation openings associated with each of the crates, and an aeration system, comprising a sensor measuring a property of the air directly above the immature phases of insects inside one of the crates of each of the clusters of crates, the sensor being connected via at least a data communication line to an air control unit;

the air control unit with a database, which database comprises a reference table with conditioned air properties in relation to one or more input parameters, wherein the one or more input parameters comprise a property of the measured air directly above the immature phases of insects inside one of the crates;

aeration devices connected to the air control unit adjacent to each of the clusters of the one or more stacks of crates, the aeration devices comprising a plurality of exit openings, the exit openings being arranged for providing airstreams over a containment volume in each of the crates through the ventilation openings associated with each of the crates, wherein the air control unit is adapted to determine from the reference table of the database appropriate conditioned air properties of the airstreams based on the one or more input parameters, and to, for each of the clusters of the one or more stacks of crates separately, set the determined appropriate conditioned air properties of the airstreams.

21. The combination according to claim 20, wherein the air control unit further comprises one or more sensors, which are arranged in the direct vicinity of the containment volume of one of the crates.

22. The combination according to claim 21, wherein the one or more sensors comprise one or more of the following: a temperature sensor, a humidity sensor, an oxygen sensor, and a carbon dioxide sensor.

23. The combination according to claim 20, wherein the plurality of exit openings are nozzles.

24. The combination according to claim 20, wherein the plurality of exit openings are horizontal slits for providing a laminar stream of air.

25. The combination according to claim 20, further comprising a heat storage device.

26. The combination according to claim 20, wherein the database further comprises a management executing system.

27. Use of a combination according to claim 20, for controlling the air climate in an insect rearing climate housing.

* * * * *